(12) United States Patent
Ahmadi et al.

(10) Patent No.: US 12,257,775 B2
(45) Date of Patent: Mar. 25, 2025

(54) 3D PRINTING HEAD FOR BIOPRINTERS

(71) Applicant: University of Prince Edward Island, Charlottetown (CA)

(72) Inventors: Ali Ahmadi, Charlottetown (CA); Ben Gregory Maccallum, Charlottetown (CA); Wyatt Norman Macnevin, Charlottetown (CA); Emad Naseri, Charlottetown (CA)

( * ) Notice: Subject to any disclaimer, the term of this patent is extended or adjusted under 35 U.S.C. 154(b) by 418 days.

(21) Appl. No.: 17/632,682

(22) PCT Filed: Aug. 7, 2020

(86) PCT No.: PCT/CA2020/051087
§ 371 (c)(1),
(2) Date: Feb. 3, 2022

(87) PCT Pub. No.: WO2021/022381
PCT Pub. Date: Feb. 11, 2021

(65) Prior Publication Data
US 2022/0274332 A1  Sep. 1, 2022

Related U.S. Application Data

(60) Provisional application No. 62/884,217, filed on Aug. 8, 2019.

(51) Int. Cl.
*B29C 64/00* (2017.01)
*B29C 64/209* (2017.01)
(Continued)

(52) U.S. Cl.
CPC .......... *B29C 64/209* (2017.08); *B29C 64/321* (2017.08); *B33Y 30/00* (2014.12); *B33Y 40/00* (2014.12); *B29K 2995/0056* (2013.01)

(58) Field of Classification Search
CPC ......... B33Y 10/00; B33Y 30/00; B33Y 70/10; B29C 64/106; B29C 64/112; B29C 64/364; B05B 14/00; B05B 14/10; B41J 2/1714
See application file for complete search history.

(56) References Cited

U.S. PATENT DOCUMENTS 5,940,674 A * 8/1999 Sachs ..................... B33Y 10/00
                                                        419/36
2010/0247703 A1* 9/2010 Shi ........................ B33Y 40/00
                                                        425/375
(Continued)

FOREIGN PATENT DOCUMENTS

CN   105647801 A   6/2016
CN   106222085 A   12/2016
(Continued)

OTHER PUBLICATIONS

Supplementary European Search Report from European Patent Application No. 20850844.0, issued Jul. 13, 2023 (all enclosed pages cited).
(Continued)

*Primary Examiner* — Thu Khanh T. Nguyen
(74) *Attorney, Agent, or Firm* — Nelson Mullins Riley & Scarborough LLP

(57) ABSTRACT

A print head for a 3D printer can receive a syringe of printing material which controllably exits through a needle or nozzle. The print head has a misting port through which a mist of the chemical cross-linker flows around the printing material for curing. The print head further includes an extraction port for extracting excess chemical cross from around the printed object.

24 Claims, 9 Drawing Sheets

(51) Int. Cl.
    *B29C 64/321*     (2017.01)
    *B33Y 30/00*     (2015.01)
    *B33Y 40/00*     (2020.01)

(56) References Cited

U.S. PATENT DOCUMENTS

| | | | | |
|---|---|---|---|---|
| 2015/0064356 | A1* | 3/2015 | Scheidt | B29C 67/246 |
| | | | | 901/43 |
| 2015/0201500 | A1* | 7/2015 | Shinar | B29C 64/112 |
| | | | | 425/132 |
| 2016/0326386 | A1* | 11/2016 | Toyserkani | B29C 64/112 |
| 2017/0232679 | A1 | 8/2017 | Gardiner et al. | |

FOREIGN PATENT DOCUMENTS

| | | |
|---|---|---|
| GB | 201902862 | 4/2019 |
| WO | 2017/081040 A1 | 5/2017 |
| WO | 2017/210663 A1 | 12/2017 |
| WO | 2018/165761 A1 | 9/2018 |
| WO | 2020/178355 A1 | 9/2020 |
| WO | 2021/022381 A1 | 2/2021 |

OTHER PUBLICATIONS

International Preliminary Report on Patentability, Chapter 1, from International Patent Application No. PCT/CA2020/051087, issued Feb. 8, 2022 (all enclosed pages cited).
International Search Report and Written Opinion from International Patent Application No. PCT/CA2020/051087, issued Nov. 2, 2020 (all enclosed pages cited).

\* cited by examiner

3D PRINTING HEAD FOR BIOPRINTERS

RELATED APPLICATIONS

This application is a 35 U.S.C. 371 national stage filing of International Application No. PCT/CA2020/051087, filed on Aug. 7, 2020, which claims the benefit of U.S. Patent Provisional Application No. 62/884,217, filed on Aug. 8, 2019. The entire contents of these applications are incorporated herein by reference in their entirety.

TECHNICAL FIELD

The current disclosure relates to 3D bioprinters and in particular to print heads for 3D bioprinters.

BACKGROUND 3D printing is an additive form of manufacturing where an object is built up from multiple layers of a printing material. There are a wide range of printing materials that can be used. Typically these materials need to be cured in some manner, whether by cooling a heated portion of the printing material, ultra-violet curing, heat curing, etc.

In biomedical and/or tissue engineering applications, the printing material may be a biologically compatible compound and is often chemically cured by chemical cross-linking. 3D bioprinting can be used for various purposes including, for example, to construct tissue scaffolds. The application of the chemical cross-linker to the printing material can be difficult to control and can result in poor printing results.

An additional, alternative and/or an improved print head for use in 3D bioprinting is desirable.

SUMMARY

In accordance with the present disclosure there is provided a misting attachment for use in a material deposition process, the misting attachment comprising: a receiver for receiving a deposition head having an exit nozzle through which a material can be deposited; a mist delivery channel in proximity to the exit nozzle of the deposition head when present, the mist delivery channel arranged to supply a flow of across-linker or suspension of particles around the material being deposited through the deposition head; and a mist extraction channel in proximity to the exit nozzle of the deposition head when present, the mist extraction channel arranged to extract a flow of excess cross-linker or suspension of particles from around the material being deposited.

In a further embodiment of the misting attachment, the mist delivery channel substantially surrounds the exit nozzle of the deposition head when present.

In a further embodiment of the misting attachment, the cavity of the mist delivery channel has an opening arranged at a downward angle promoting 360° laminar flow of the atomized cross-linker or suspension of particles around the exit nozzle of the deposition head when present.

In a further embodiment of the misting attachment, the deposition head is a print head for a 3D printing process.

In a further embodiment of the misting attachment, the extraction channel substantially surrounds the exit nozzle of the print head when present.

In a further embodiment, the misting attachment further comprises an extraction profile on a surface of the attachment between the extraction channel and the exit nozzle of the print head when present.

In a further embodiment of the misting attachment, the extraction profile has an arcuate profile surrounding the exit nozzle of the print head when present.

In a further embodiment of the misting attachment, the receiver is adapted to be releasably secured to the print head.

In a further embodiment of the misting attachment, the print head comprises one of a syringe, and a dispensing needle.

In a further embodiment of the misting attachment, the deposition head comprises a droplet deposition head.

In a further embodiment of the misting attachment, the extraction channel is spaced apart down stream from the mist delivery channel by a predetermined distance to expose material droplets deposited from the deposition head to the cross-linker or suspension of particles for a sufficient amount of time.

In a further embodiment of the misting attachment, the mist delivery channel supplies the flow of atomized cross-linker or suspension of particles 360° around the material being deposited by the deposition head.

In a further embodiment, the misting attachment further comprises a plurality of mist delivery channels arranged circumferentially around the exit nozzle.

In a further embodiment of the misting attachment, each of the plurality of mist delivery channels are in fluid communication with each other.

In a further embodiment, the misting attachment further comprises a supply connection port for connecting the mist delivery channel to the supply of atomized cross-linker or suspension of particles.

In accordance with the present disclosure there is further provided a misting attachment system for a material deposition process comprising: a misting attachment comprising: a receiver for receiving a deposition head having an exit nozzle through which a material can be deposited; a mist delivery channel in proximity to the exit nozzle of the deposition head when present, the mist delivery channel arranged to supply a flow of across-linker or suspension of particles around the material being deposited through the deposition head; and a mist extraction channel in proximity to the exit nozzle of the deposition head when present, the mist extraction channel arranged to extract a flow of excess cross-linker or suspension of particles from around the material being deposited; an ultrasonic atomizer within a misting chamber connected to the mist delivery channel for providing the atomized cross-linker or suspension of particles; a vacuum pump connected to the mist extraction channel to provide suction for extracting excess cross-linker or suspension of particles.

In a further embodiment, the misting attachment system further comprises an air pump connected to the misting chamber to supply the flow of atomized cross-linker or suspension of particles.

In a further embodiment of the misting attachment system, the mist delivery channel substantially surrounds the exit nozzle of the deposition head when present.

In a further embodiment of the misting attachment system, the cavity of the mist delivery channel has an opening arranged at a downward angle promoting 360° laminar flow of the atomized cross-linker or suspension of particles around the exit nozzle of the print head when present.

In a further embodiment of the misting attachment system, the deposition head is a print head for a 3D printing process.

In a further embodiment of the misting attachment system, the extraction channel substantially surrounds the exit nozzle of the print head when present.

In a further embodiment, the misting attachment system further comprises an extraction profile on a surface of the attachment between the extraction channel and the exit nozzle of the print head when present.

In a further embodiment of the misting attachment system, the deposition head comprises a droplet deposition head.

In a further embodiment of the misting attachment system, the extraction channel is spaced apart down stream from the mist delivery channel by a predetermined distance to expose material droplets deposited from the deposition head to the cross-linker or suspension of particles for a sufficient amount of time.

BRIEF DESCRIPTION OF THE DRAWINGS

Further features and advantages of the present disclosure will become apparent from the following detailed description, taken in combination with the appended drawings, in which.

DETAILED DESCRIPTION 3D bioprinting of materials can use a chemical cross-linking agent that hardens the printed material after being extruded from the print head. A print head attachment is described further below that allows the cross-linker to be supplied as a mist to the extruded printing material and any excess cross-linker extracted from around the print head. Extracting excess cross-linker helps prevent or reduce print errors that can result from a buildup of excess cross linker around the printing area. The print head attachment can be attached to existing print heads without requiring significant changes to the 3D printer.

FIG. 1 depicts components of a 3D bioprinter incorporating a 3D print head attachment system. The 3D bioprinter 100 has a print head assembly that includes a print head 102 and a print head attachment 104. The print head assembly may be secured to an XY positioning assembly 106 by a print head mount 108. A printing material can be controllably extruded 108 from the print head 102 onto a print stage 110 to additively form a printed object 112. The print stage 110 may be connected to a Z positioning assembly 114 to raise/lower the print stage 110 as the object 112 is printed. It will be appreciated that the XY positioning assembly 106 and the Z positioning assembly 114 provide relative movement between the print stage 110 and the print head 102. Although depicted as moving the print head in the XY direction and the print stage in the Z direction, the positioning assemblies may be connected in various arrangements to provide the relative movement between the print head and print stage.

The print head may be provided by, for example a syringe, a Luer-Lock dispensing needles, etc. The print head may be controlled by various means including pneumatically by a compressed air source 116, mechanically by a motor or other types of actuators. The print head may be filled with a print material that is extruded, or otherwise deposited, on the print stage to form the object. The printing material may be selected from a wide range of materials that are cured, or hardened, by contact with another chemical, referred to as a cross-linker. The particular cross-linker used may vary depending upon the printing material used. For example, the printing material may be sodium alginate, chitosan, collagen, agarose, or other compatible biomaterial and/or hydrogels. The cross-linker may include, for example, calcium chloride (calcium ion), genipin, aldehydes or other chemicals capable of cross-linking the printing material.

As depicted in FIG. 1, the print head attachment 104 may be fit over, or attached to, the print head 102 so that the print material exiting the print head at an exit nozzle of the print head passes through the print head attachment. Although depicted as exiting the print head 102 within the print head attachment, it is possible for the exit nozzle of the print head may extend past a bottom of the print head attachment. The temperature of the print material being extruded may be controlled, for example temperatures may range between 4°-20° C. The temperature of the print material may change the material's viscosity for improved control over the printability as well as control of the diffusion of crosslinking ions.

The print head attachment 102 comprises a mist delivery channel 118 that supplies a mist of the chemical cross-linker around the extruded print material 108. The mist delivery channel 118 may be connected to a mist supply port 120 that allows the mist delivery channel to be connected to a mist supply source 122, for example by a tube or tubing. The mist supply source 120 may comprises a tank holding the cross-linker solution. An ultrasonic atomizer 124 may be used to generate a mist of cross-linker droplets 126. An air pump 128 may be used to supply a flow of the mist of cross-linker to the mist delivery channel 118. The droplets generated may vary in size, however for calcium chloride used to cross-link sodium alginate a diameter of approximately 10-100 microns in size may be used. Similarly, various flow rates of the cross-linker mist may be provided by the air pump 128 at a rate of about 1 L/min (air and droplets mixed). The mist of cross linker is supplied to the mist delivery channel 118 that supplies the cross-linker to around the extruded print material. The mist delivery channel is located in proximity to the exit nozzle of the print head when present so that the mist delivery channel supplies a flow of atomized cross-linker around the printing material extruded through the print head. The mist delivery channel 118 may have an exit opening to promote laminar flow of the cross-linker mist about the extruded print material.

In order to prevent excess cross-linker from contacting the printed object or possibly pooling on the print stage, the print head attachment further includes an extraction channel 130 that extracts excess cross-linker from the print area. The extraction channel 130 may have an extraction connection port 132 that can be connected to a vacuum pump 134 to provide sufficient suction to extract the excess cross-linker which may be collected in a waste tank 136, or possibly resupplied to the cross-linker solution tank 122. Although the extraction flow rate may vary, a flow rate of about 3-5

L/min may be sufficient to extract enough cross-linker to prevent or reduce pooling of the cross-linker. The extraction channel enables even removal of the excess cross-linker without disrupting the interaction between the cross-linker and the extruded print material.

Figure 1:
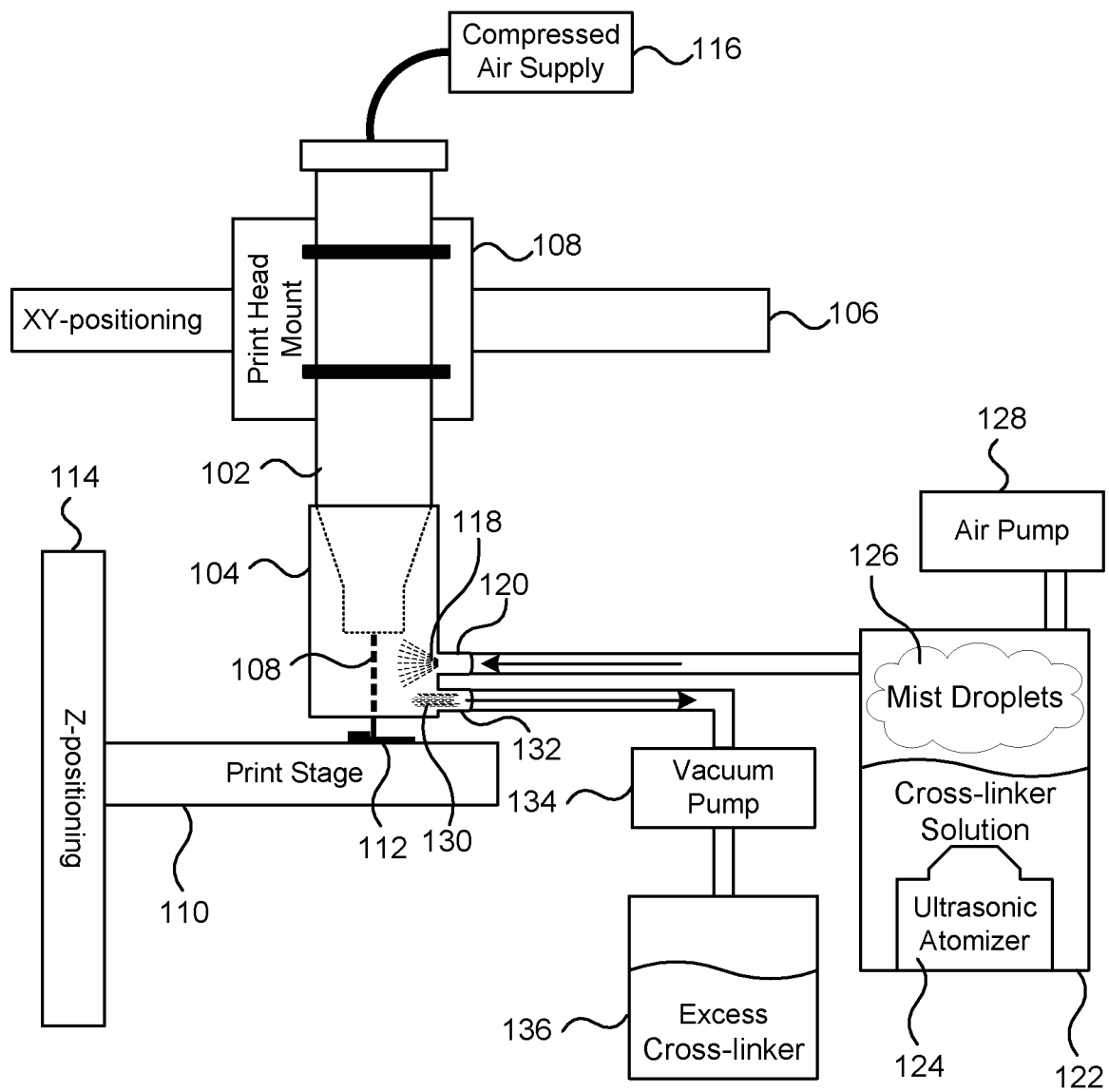
FIG. 1 depicts components of a 3D bioprinter incorporating a 3D print head attachment system.
Figure 2B:
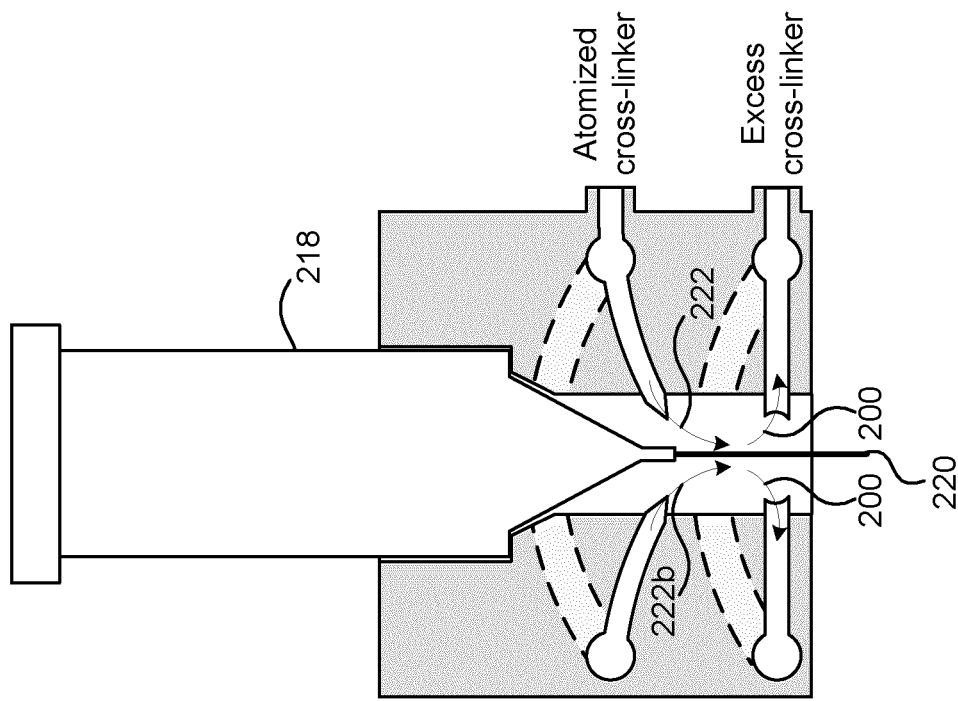
FIG. 2B depicts the 3D print head attachment of FIG. 2A in use.
Figure 2A:
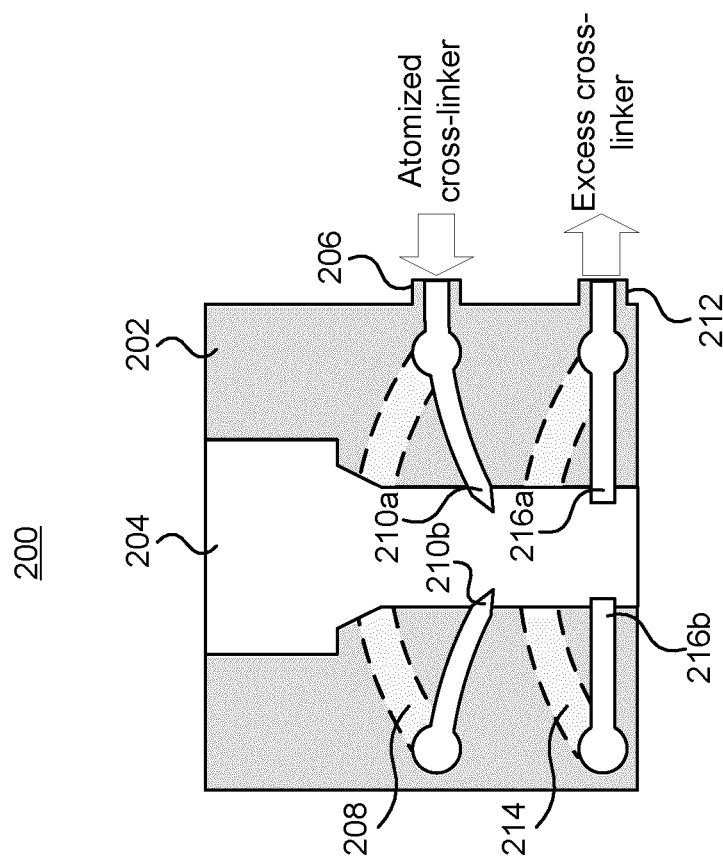
FIG. 2A depicts an illustrative 3D print head attachment.

FIG. 2A depicts an illustrative 3D print head attachment. The print head attachment 104 was described above as having mist delivery channel with a single opening in proximity to the extruded material. It is desirable to promote flow of the cross-linker around the entirety of the extruded print material and as such a plurality of mist openings may be provided in proximity to the extruded material. The print head attachment 200 comprises a body 202, which may be formed from various materials including both plastics and metals. The body 202 comprises a receiver opening 204 for receiving the print head. The receiver opening 204 may secure the attachment to the print head, for example by a friction fit, or an additional securing mechanism (not depicted) may be used. The particular shape of the receiver may depend upon the shape and size of print head used, however it generally comprises an opening into which the print head can be received that continues through the body to allow the print material to be extruded from the print head onto the print stage.

The body may include a mist connector 206 for securing tubing to in order to supply the mist of cross-linker. The mist connector 206 may be connected to a mist delivery channel 208 surrounding the receiver opening in the body 202. A plurality of delivery openings 210a, 210b may be connected to the delivery channel about the receiver opening in order to supply the mist of cross-linker around extruded print material. The print head attachment may further comprise an extraction connector 212 for connecting the attachment to a vacuum pump. The extraction connector 212 may be connected to an extraction channel 214 surrounding the receiver opening 204. A plurality of extraction openings 216a, 216b may be connected to the extraction channel about the receiver opening 204 in order to extract excess cross-linker from the print area.

FIG. 2B depicts the 3D print head attachment of FIG. 2A in use. Elements of the print head attachment described above with reference to FIG. 2A are not labelled in FIG. 2B for clarity of the drawing. As depicted, print head, which may be a syringe filled with the printing material, is received within the receiver opening 204 in the attachment body 202 and is secured to the attachment. The print head controllably extrudes print material 220 to form a desired shape. Atomized cross-linker flows through the connection port 206, into the delivery channel 208 and out of the delivery openings 210a, 210b. The flow of cross linker depicted by arrows 222a, 222b flows out of the openings and surrounds the extruded print material 220 causing cross links to be formed. Excess cross linker is extracted by a vacuum pump connected to the extraction connection port 212. The excess cross linker is extracted through the plurality of extraction openings 216a, 216b in the extraction channel 214.

Figure 3:
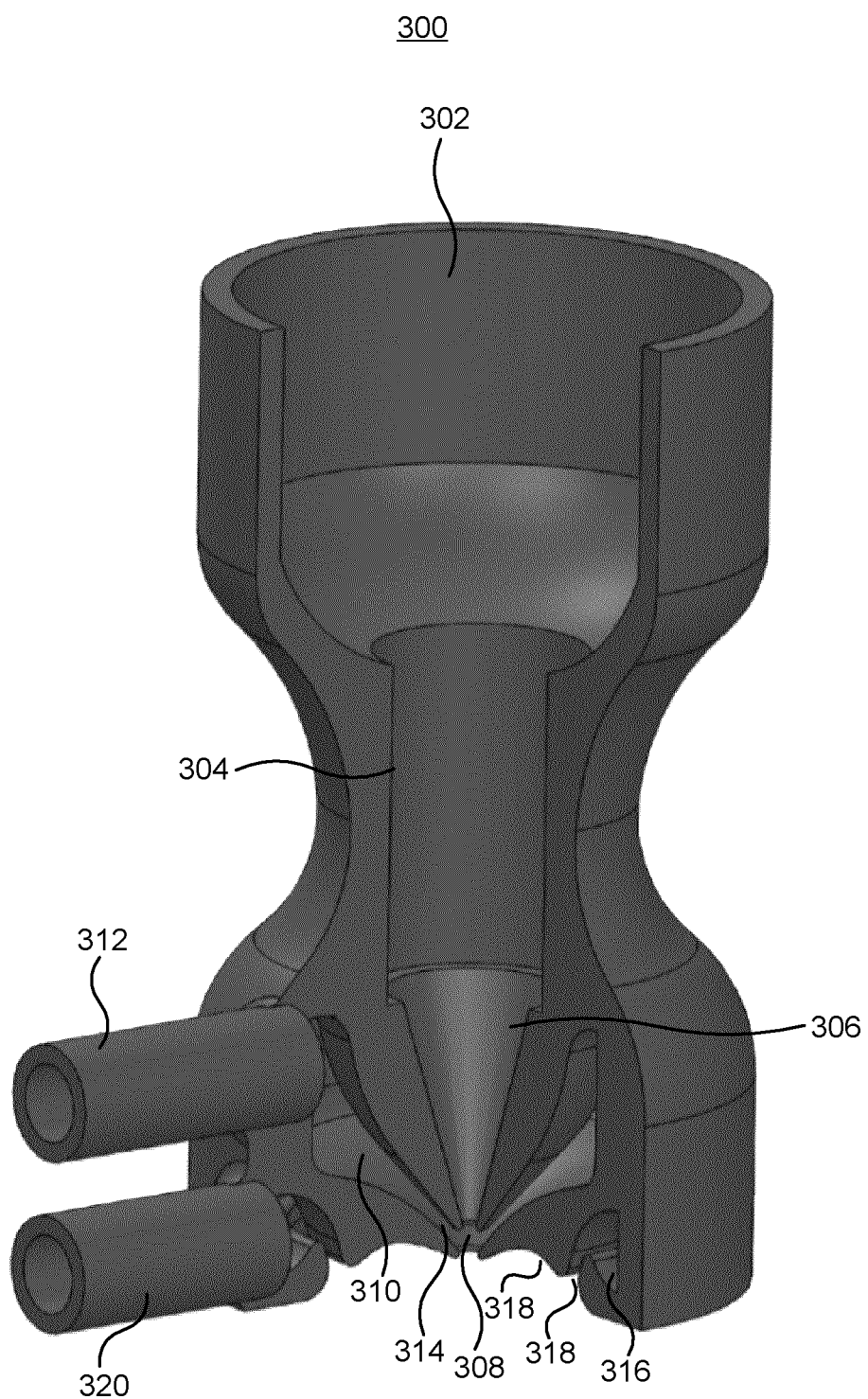
FIG. 3 depicts a further illustrative 3D print head attachment.

FIG. 3 depicts a further illustrative 3D print head attachment. The print head attachment described above with regard to FIGS. 2A and 2B may provide acceptable printing results, however the mist delivery channel and openings as well as the extraction channel and openings may not provide desired printing results. The print head attachment described further below with reference to FIG. 3 and FIG. 4 has an improved shape of the mist delivery channel for promoting the laminar flow of the cross-linker mist 360° about the extruded print material. Similarly, the print head attachment has an improved shape of the mist extraction channel to reduce disruption of the laminar flow of the cross-linker mist about the extruded print material while still removing the excess cross-linker from the print area.

The print head attachment 300 may be formed as a single unitary piece of material having various channels and openings formed within it. The print head attachment may be formed using various manufacturing techniques including 3D printing and injection molding. The particular shape and size of the print head attachment may be varied according to the particular print head the attachment is designed for.

The print head attachment 300 has a receiver opening 302 into which a print head, such as a syringe can be received. The receiver opening 302 continues through the body as cylindrical body opening 304 for receiving a portion of the print head. The receiver opening and body opening may continue through a conical opening portion 306 for receiving a portion of the print head, such as a cone-tip needle attachment. The exit nozzle of the print head may extend through the conical opening and through an exit opening 308. The exit nozzle of the print head may extend fully through the exit opening 308, or it may remain within the exit opening 308, or even within the conical opening 306.

The print head attachment 300 comprises a mist delivery channel 310. The delivery channel may be formed about a vertical axis of the body to provide a continuous 360° channel. The delivery channel 310 is connected to a delivery connection port 312 that allows a tube or hose to be connected to the print head attachment for providing a flow of cross-linker mist into the delivery channel 310. The delivery channel 310 is in proximity to the exit nozzle of the print head when it is present, and supplies a flow of atomized cross-linker around the printing material extruded through the print head. The delivery channel 310 is depicted as having a substantially continuous opening 314 that substantially surrounds the exit opening 308, however, it is possible to provide a plurality of discreet openings surrounding the exit opening 308. The delivery channel 310 may have a cross sectional profile that descends downward at an angle of between 30-45° toward the delivery opening 314 to impart downward movement to the mist flow and promote laminar flow about the extruded print material. As depicted, the channel profile may have an enlarged upper chamber with the connection port 312 located towards a top of the enlarged upper chamber, which may help provide a better flow of cross-linker out of the delivery opening 314.

The print head attachment 300 further comprises a mist extraction channel 316 that extracts excess cross-linker from the print area. Similar to the delivery channel, the extraction channel 316 may be formed about the vertical axis of the body to provide a continuous 360° channel. The extraction channel 316 is arranged in proximity to the exit nozzle of the print syringe when present to extract a flow of excess cross-linker from around the extruded printing material. The extraction channel 316 may have a substantially continuous extraction opening 318 that that substantially surrounds the exit opening 308, however, it is possible to provide a plurality of discreet extraction openings surrounding the exit opening 308. The extraction opening may be spaced apart circumferentially from the exit opening 308. The bottom surface of the attachment between the extraction opening 318 and the exit opening 308 may have an arcuate profile 320 for helping with the extraction of excess cross linker from the print area. An extraction connection port 322 is connected to the extraction channel and allows a vacuum pump to be connected in order to extract the excess cross linker.

Figure 4:
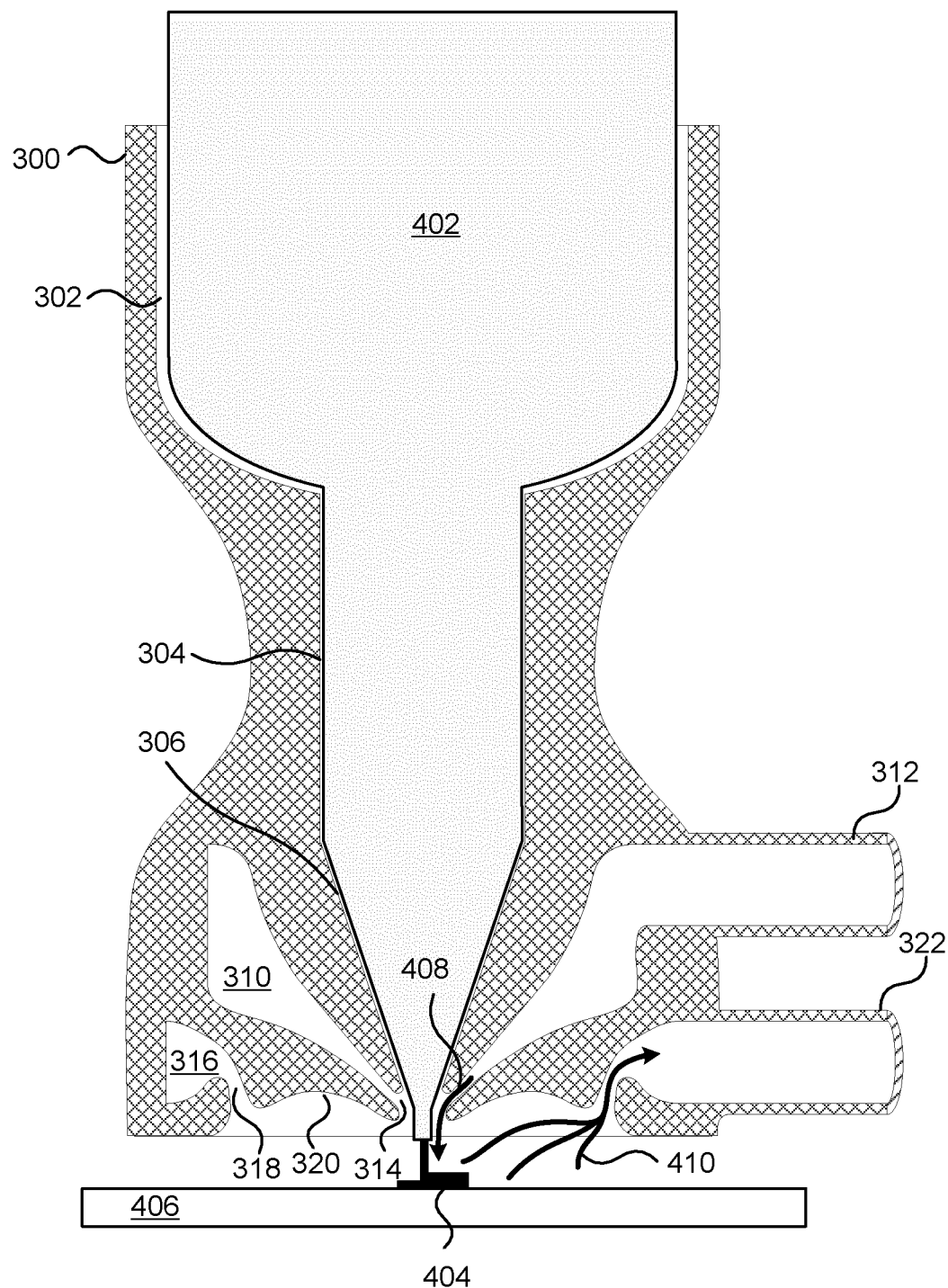
FIG. 4 depicts a cross section of the print head attachment of FIG. 3.

FIG. 4 depicts a cross section of the print head attachment of FIG. 3. A print head 402 is received within the opening 302, cylindrical body opening 304, conical opening 306, and through the exit opening 308. As depicted, the exit nozzle of the print head extends past the exit opening, however the exit nozzle may remain within the print head attachment. The print head is controlled to extrude the printing material 404 onto a printing platform 406. As the printing material is extruded through the exit nozzle of the print head, the printing material is contacted with a flow of cross-linker mist, depicted by arrow 408. The mist of cross-linker is supplied through the connection port 312 into the delivery channel 310 and out the delivery opening 314 located in proximity to the nozzle exit. The shape of the delivery channel 310 helps to promote a laminar flow of the cross-linker mist down and around the printing material as it is extruded. The excess cross-linker mist that remains in the print area is extracted by the extraction channel 316 as depicted by arrows 410 through the extraction opening 318. The extraction profile 320 at the bottom of the print head attachment may help to extract the excess cross-linker without disturbing the flow of the cross-linker around the extruded printing material.

A print head attachment system as described above can be easily connected to existing print heads. The print heads may print an object by extruding a filament of a printing material. The extruded filament may have a wide range of sizes, such as for example between about 20 microns and about 2000 microns. The print material may include various compounds or materials including for example, living cells, micro particles, nano particles, etc. The print head attachment can improve the printing results when printing with print materials that are exposed to cross-linkers or other coating particles. The cross-linker may be delivered in the form of atomized mist droplets. The print head attachment may be used with sodium alginate as the print material, using calcium chloride ($CaCl_2$)) as the crosslinking agent to form a solid thermoset elastomer, calcium alginate. The print head attachment may be used with other print materials and crosslinking agents. Ultrasonic atomization of the cross linker creates a fine mist of droplets externally from the attachment that can be delivered to the attachment using forced airflow. The droplets of crosslinking agent are provided into a cavity that is designed to promote 360° laminar flow of mist about the needle tip that is focused directly on the extruded biomaterial. Excess droplets of the cross linker may be removed with an external vacuum pump. The attachment may fit directly onto common bioprinting equipment such as syringes and Luer-Lock dispensing needles. Mist removal may be enabled via a cavity that features a narrow channel to promote even removal of the excess mist to reduce the disruption of interaction between droplets of the crosslinking agent and the print material being extruded. The extraction flow rate may be set at between 3-5 L/min. Droplets of the cross linking agent may be generated in the diameter range of 10-100 microns using an ultrasonic atomizing system and forced into the print head at ~1 L/min (air and droplets, mixed) by an air pump. The temperature of the printing material may be controlled, for example within a temperature range of between 4-20° C., which may change viscosity of the printing material for improved printability and may enable improved diffusion of crosslinking ions. The attachment may fit directly onto common bioprinting equipment such as syringes and Luer-Lock dispensing needles.

Figure 5:
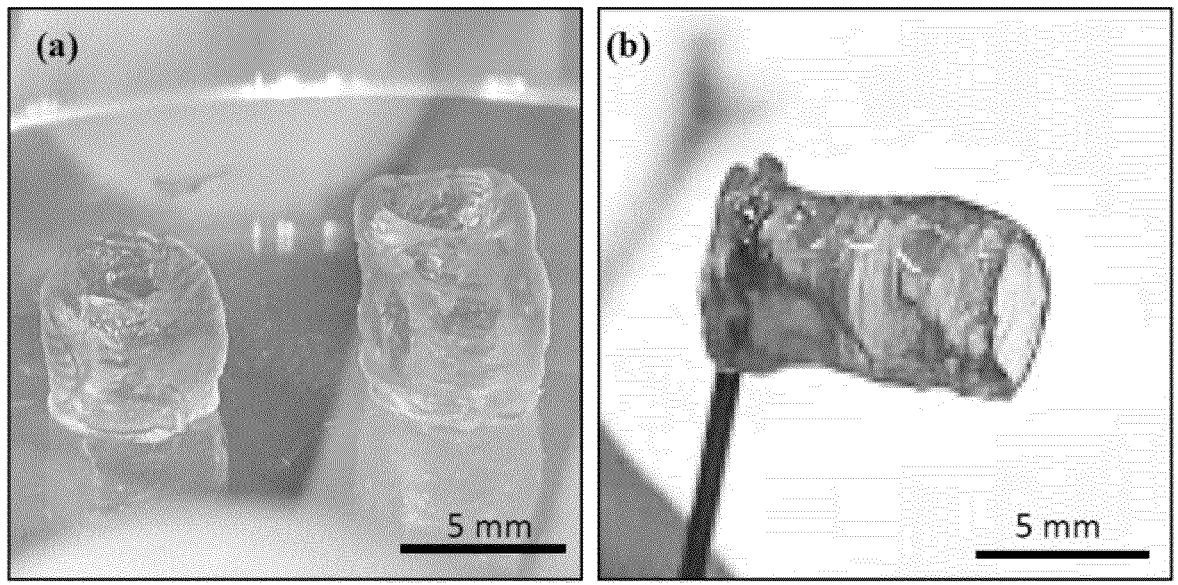
FIG. 5 depicts a 3D printed structure.

FIG. 5 shows photographs of a 3D printed cylindrical constructs. One cylindrical construct 502 was printed with 5 wt % sodium alginate using 10 wt % $CaCl_2$ mist with a flow rate of 750 mL/min from a misting attachment in accordance with the current disclosure. A second cylindrical construct 504 was printed with 7 wt % sodium alginate using 10 wt % $CaCl_2$ mist from a misting attachment in accordance with the current disclosure. Both cylindrical constructs exhibited strong layer adhesion.

Figure 6:
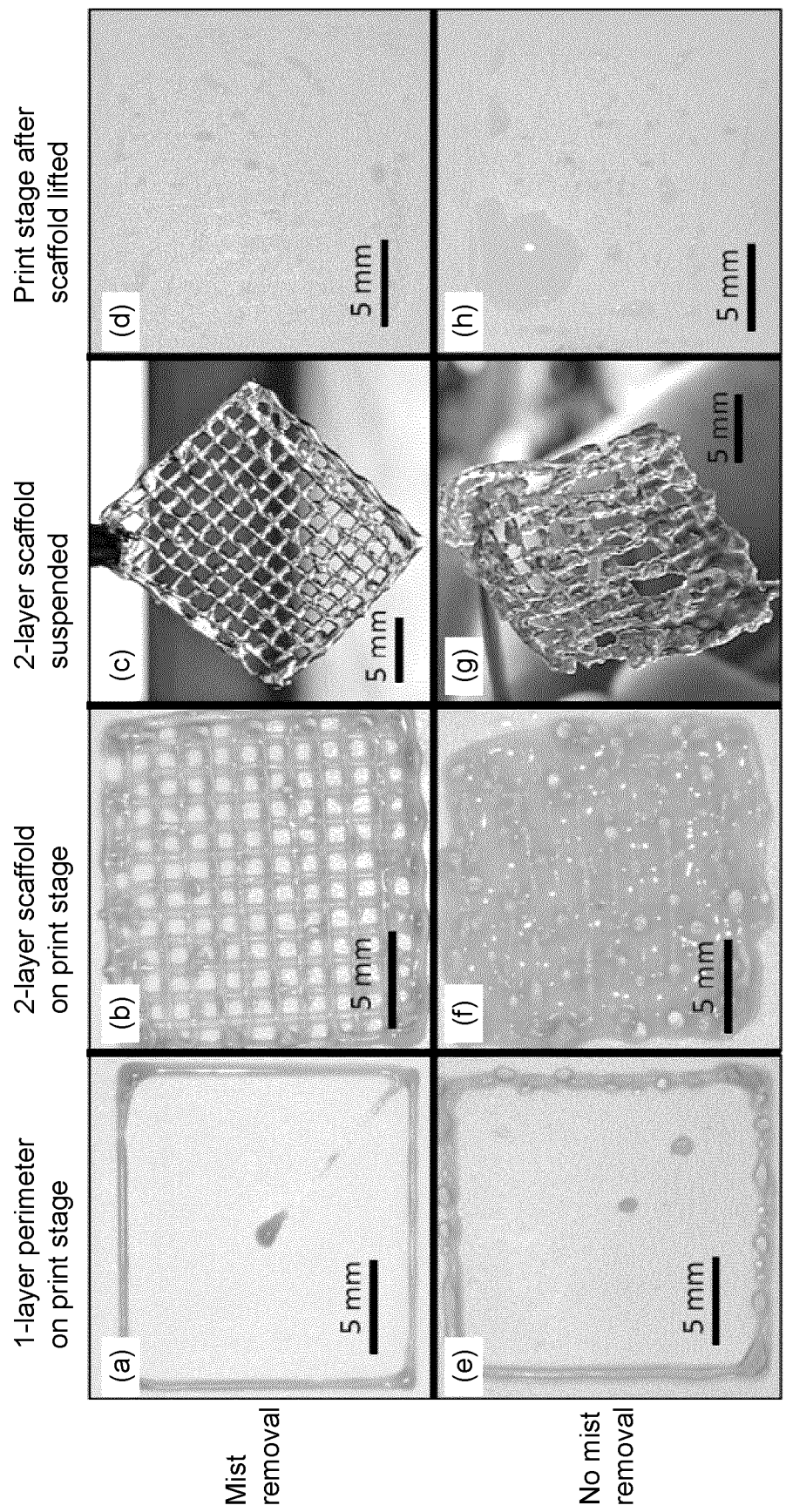
FIG. 6 depicts a comparison of 3d printing results with mist removal and without mist removal.

FIG. 6 shows photographs of 3D printing results with and without mist removal using a misting attachment in accordance with the current disclosure. All other parameters of the printing remained the same and used 5 wt % sodium alginate and 10 wt % $CaCl_2$ mist. As can be seen in the comparison between print results depicted in panels (a) and (e), panels (b) and (f) and panels (c) and (g), the use of the mist removal during printing results in a higher quality print. Although not wishing to be bound by theory, it is believed that the higher quality print results are, at least in part, a result of no or little liquid accumulation on the print stage when using the mist removal as can be seen in comparison of panels (d) and (h). The print head attachment and system has been described above with particular reference to supplying an atomized mist of a cross-linker around extruded print material. The same print head attachment and system may also be used with materials other than cross-linkers. For example, the mist drops may contain the cross-linker as described above, or may contain suspensions of other particles and liquids such as a coating to be applied to the extruded material. The particles may be the cross-linker as described above, or may be other particles such as a coating to be applied to the extruded material. The coating particles may provide various functionality such as a lubricant, an adhesive, a colorant, or other particles provide desired functionality. Further, the atomized mist supplied around the print material may include a combination of particles such as cross-linkers and coatings. The attachment may be used in various applications including fabricating tissue constructs using biocompatible polymers including sodium alginate in fabricating vascular and liver tissue, collagen in fabricating skin tissue and agarose and chitosan for various tissue engineering applications. Further, the above has described the print head attachment with respect to its use with extrusion based 3D printing. As described further below, a similar attachment may be used with other deposition processes in addition to, or as an alternative to, extrusion based 3D printing.

Droplet-based deposition techniques can be used both as a 3D printing techniques as well as for other applications, including in pharmaceutical development, high-throughput chemical processes, etc. Droplet based deposition techniques may be used for 3D bioprinting and enables precise deposition of biocompatible polymers and living cells, which may be referred to as bioinks, to fabricate complex in-vitro tissue models.

Existing systems crosslink bioink droplets after printing to form rigid structures; however, crosslinking after printing may result in too rapid gelation of the droplets as a result of too much crosslinker or too slow gelation of the droplets. Too rapid or too slow gelation can lead to poor adhesion or shape fidelity, respectively. Furthermore, improper gelation can inhibit cell proliferation. The fabrication of complex tissue and organ constructs by, for example, depositing living tissue spheroids may be limited by the rate and extent of fusion the deposited spheroids, which in turn may depend upon the gelation rate. A misting attachment similar to that described above may be used to facilitate the crosslinking of printed bioink droplets before deposition onto the print stage, offering controllable proper gelation of the bioink.

Figure 7:
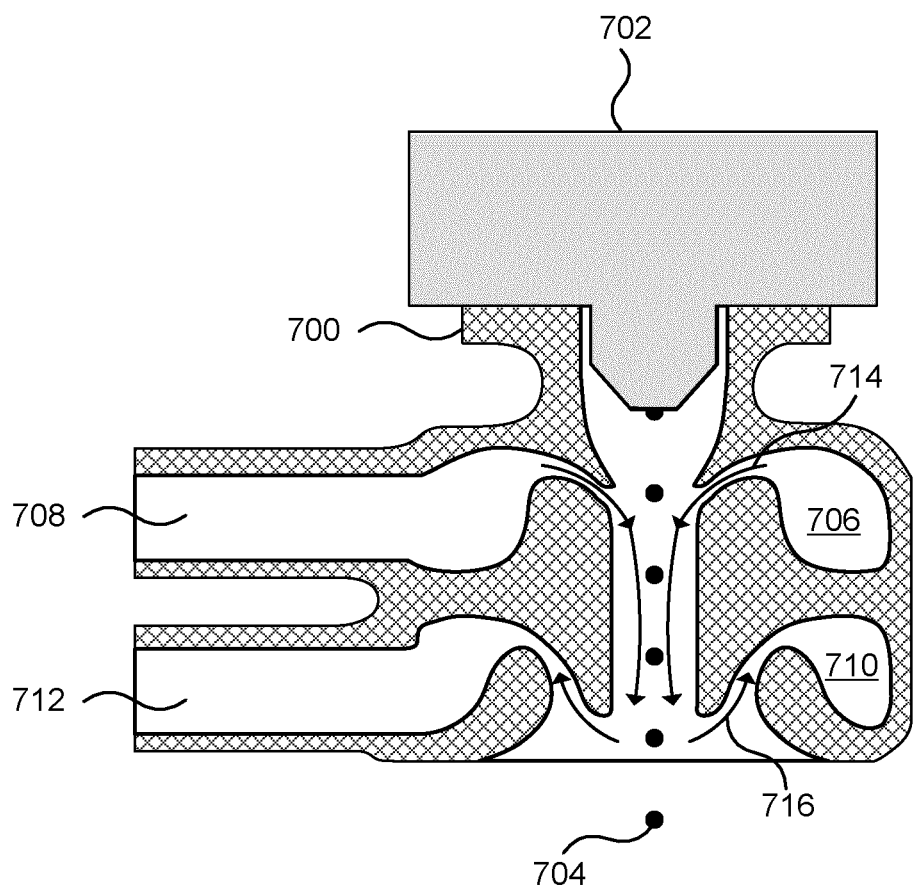
FIG. 7 depicts an alternative misting attachment.
Figure 8:
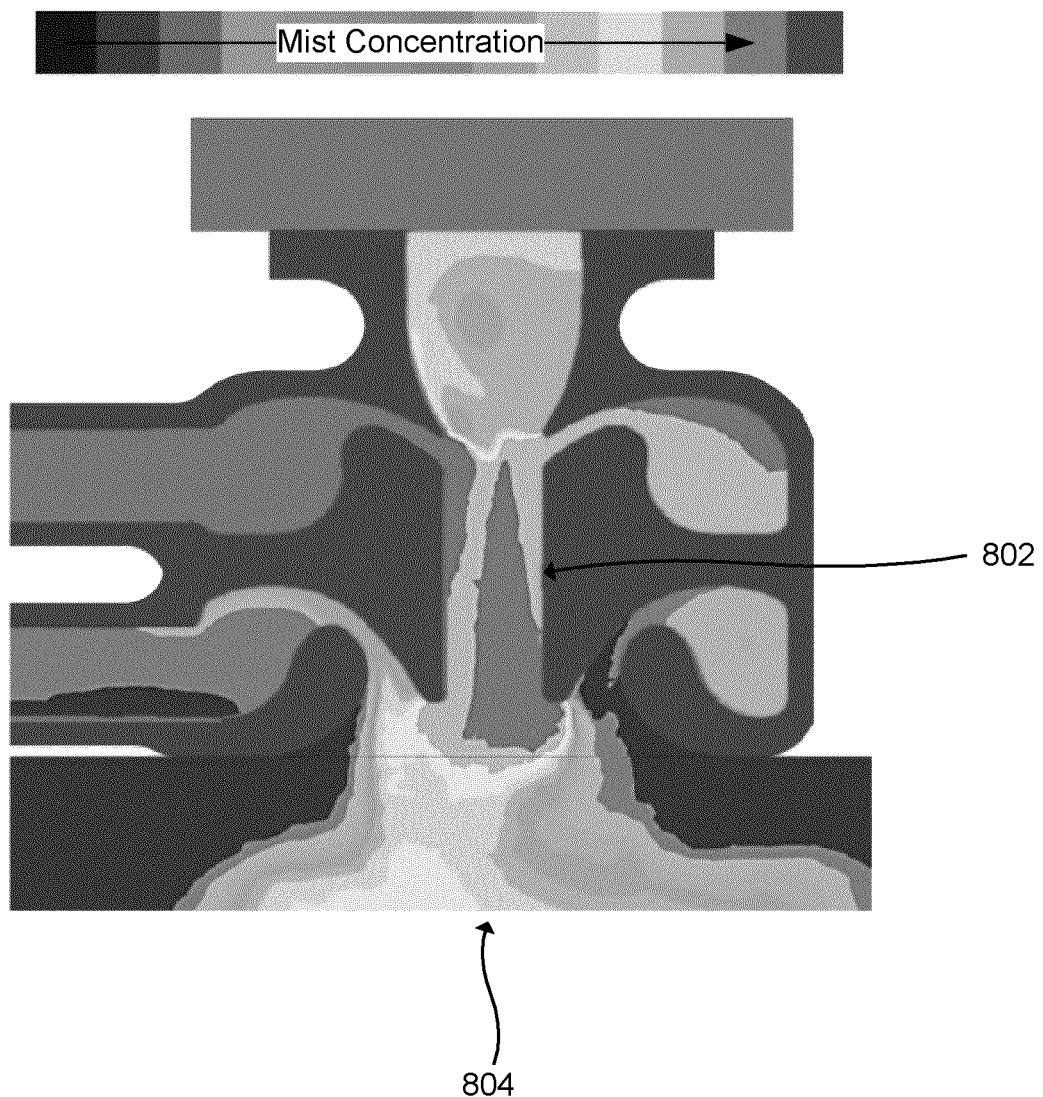
FIG. 8 depicts simulation results of mist concentration in the misting attachment of FIG. 7.
Figure 9:
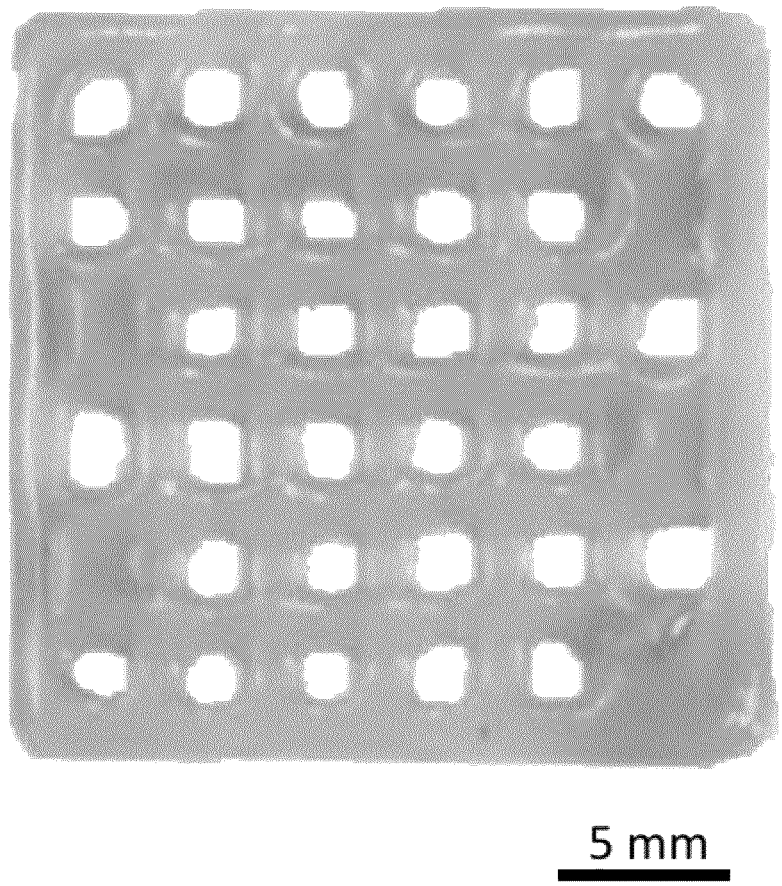
FIG. 9 depicts a structure printed using droplet-based deposition using the misting attachment of FIG. 7.

FIG. 7 depicts a misting attachment for a droplet-based deposition process. The misting attachment 700 is similar to the print head attachment described above. The misting attachment 700 may be attached to, or otherwise coupled to, a droplet deposition head 702 that deposits drops of material 704 onto a surface (not shown). The misting attachment 700 comprises a mist delivery channel 706 that delivers a supply of mist of crosslinker, or other suspensions of particles, around the droplets as they pass through the attachment. The mist delivery channel 706 may be connected to a delivery port 708 that can be used to provide a flow of the mist, whether it is a crosslinker, which could be atomized, or other suspensions of particles. The attachment 700 further comprises a mist extraction channel 710 through which excess mist can be extracted. The extraction channel 710 may be connected to an extraction port 712 that can provide a vacuum to extract the excess mist. The mist may enter a channel through which material droplets are deposited, as depicted by arrows 714 and then be extracted away from the droplets 704 as they are deposited as depicted by arrows 716.

FIG. 8 depict simulation results of mist concentration within a misting attachment in accordance with the misting attachment of FIG. 7. As depicted, the mist concentration is high in a path that the deposited droplets pass 802 prior to being extracted through the mist extraction channel. The concentration of the mist below the attachment is relatively low. The length between the mist delivery channel and the mist extraction channel can be set so that the material droplets are exposed to the mist for an appropriate length of time. The appropriate length of time may depend upon the material being deposited, the misting agent, as well as the desired properties, such as gelation amount, coating amount, etc. for a particular application. In addition to the length between the mist delivery channel and the mist extraction channel, the flow rate and concentration of the mist may also be varied to adjust exposure levels to a desired or appropriate amount.

The misting attachment may direct the flow of mist to provide even, 360-degree contact with the droplets as they are deposited. The geometry of the attachment may provide a uniform mist concentration on the centerline of the attachment, or through the path of the deposited droplets. The mist flowrate and concentration may be adjusted to modify the extent of exposure which may adjust the crosslinking rate. Adjusting the flowrate and concentration may be used to control the mechanical properties of the deposited materials. The temperature of the bioink may be adjusted (4-37° C.) to improve diffusion of the crosslinker mist if desired.

The crosslinker, or the suspended particles, may be collected within the attachment device to prevent accumulation of liquid on the print stage. The geometry of the outlet channel may prevent disruption to the printed droplets as they exit the attachment.

The misting attachment for droplet-based deposition techniques may be used in a variety of applications, including for example, fabricating tissue spheroids for in-vitro tissue and organ regeneration, printing or otherwise manufacturing biocompatible beads for drug delivery, coating bioprinted droplets with functional substances (i.e. conductive, hydrophilic, hydrophobic).

FIG. 9 depicts a porous scaffold printed using the misting attachment described above with reference to FIG. 7. The droplet based printing process used a 3 wt % sodium alginate with a crosslinking misting agent of 10 wt % $CaCl_2$. As depicted the scaffold exhibits high shape fidelity and has good co-droplet adhesion.

It will be appreciated by one of ordinary skill in the art that the system and components shown in FIGS. 1-9 may include components not shown in the drawings. For simplicity and clarity of the illustration, elements in the figures are not necessarily to scale, are only schematic and are non-limiting of the elements structures. It will be apparent to persons skilled in the art that a number of variations and modifications can be made without departing from the scope of the invention as defined in the claims.

What is claimed is:

1. A misting attachment for use in a material deposition process, the misting attachment comprising:

a receiver for receiving a deposition head having an exit nozzle through which a material can be deposited;

a mist delivery channel in proximity to the exit nozzle of the deposition head when present, the mist delivery channel arranged to supply a flow of a cross-linker or suspension of particles around the material being deposited through the deposition head; and a mist extraction channel in proximity to the exit nozzle of the deposition head when present, the mist extraction channel arranged to extract a flow of excess cross-linker or suspension of particles from around the material being deposited.

2. The misting attachment of claim 1, wherein the mist delivery channel substantially surrounds the exit nozzle of the deposition head when present.

3. The misting attachment of claim 2, wherein the cavity of the mist delivery channel has an opening arranged at a downward angle promoting 360° laminar flow of the atomized cross-linker or suspension of particles around the exit nozzle of the deposition head when present.

4. The misting attachment of claim 1, wherein the deposition head is a print head for a 3D printing process.

5. The misting attachment of claim 4, wherein the extraction channel substantially surrounds the exit nozzle of the print head when present.

6. The misting attachment of claim 5, further comprising an extraction profile on a surface of the attachment between the extraction channel and the exit nozzle of the print head when present.

7. The misting attachment of claim 6, wherein the extraction profile has an arcuate profile surrounding the exit nozzle of the print head when present.

8. The misting attachment of claim 4, wherein the receiver is adapted to be releasably secured to the print head.

9. The misting attachment of claim 8, wherein the print head comprises one of a syringe, and a dispensing needle.

10. The misting attachment of claim 1, wherein the deposition head comprises a droplet deposition head.

11. The misting attachment of claim 10, wherein the extraction channel is spaced apart down stream from the mist delivery channel by a predetermined distance to expose material droplets deposited from the deposition head to the cross-linker or suspension of particles for a sufficient amount of time.

12. The misting attachment of claim 1, wherein the mist delivery channel supplies the flow of atomized cross-linker or suspension of particles 360° around the material being deposited by the deposition head.

13. The misting attachment of claim 1, further comprising a plurality of mist delivery channels arranged circumferentially around the exit nozzle.

14. The misting attachment of claim 11, wherein each of the plurality of mist delivery channels are in fluid communication with each other.

15. The misting attachment of claim 1, further comprising a supply connection port for connecting the mist delivery channel to the supply of atomized cross-linker or suspension of particles.

16. A misting attachment system for a material deposition process comprising:
a misting attachment comprising:
a receiver for receiving a deposition head having an exit nozzle through which a material can be deposited;
a mist delivery channel in proximity to the exit nozzle of the deposition head when present, the mist delivery channel arranged to supply a flow of a cross-linker or suspension of particles around the material being deposited through the deposition head; and
a mist extraction channel in proximity to the exit nozzle of the deposition head when present, the mist extraction channel arranged to extract a flow of excess cross-linker or suspension of particles from around the material being deposited;
an ultrasonic atomizer within a misting chamber connected to the mist delivery channel for providing the atomized cross-linker or suspension of particles;
a vacuum pump connected to the mist extraction channel to provide suction for extracting excess cross-linker or suspension of particles.

17. The misting attachment system of claim 16, further comprising an air pump connected to the misting chamber to supply the flow of atomized cross-linker or suspension of particles.

18. The misting attachment of claim 16, wherein the mist delivery channel substantially surrounds the exit nozzle of the deposition head when present.

19. The misting attachment of claim 18, wherein the cavity of the mist delivery channel has an opening arranged at a downward angle promoting 360° laminar flow of the atomized cross-linker or suspension of particles around the exit nozzle of the print head when present.

20. The misting attachment of claim 16, wherein the deposition head is a print head for a 3D printing process.

21. The misting attachment of claim 20, wherein the extraction channel substantially surrounds the exit nozzle of the print head when present.

22. The misting attachment of claim 21, further comprising an extraction profile on a surface of the attachment between the extraction channel and the exit nozzle of the print head when present.

23. The misting attachment of claim 16, wherein the deposition head comprises a droplet deposition head.

24. The misting attachment of claim 23, wherein the extraction channel is spaced apart down stream from the mist delivery channel by a predetermined distance to expose material droplets deposited from the deposition head to the cross-linker or suspension of particles for a sufficient amount of time.

* * * * *